US009963419B2

(12) United States Patent
Kuvadia et al.

(10) Patent No.: US 9,963,419 B2
(45) Date of Patent: May 8, 2018

(54) PROCESS FOR IN SITU WATER REMOVAL FROM AN OXIDATIVE ESTERIFICATION REACTION USING A COUPLED REACTOR-DISTILLATION SYSTEM

(71) Applicants: Dow Global Technologies LLC, Midland, MI (US); ROHM AND HAAS COMPANY, Philadelphia, PA (US)

(72) Inventors: Zubin B. Kuvadia, Pearland, TX (US); Kirk W. Limbach, Dresher, PA (US); Dmitri A. Kraptchetov, Lansdale, PA (US); Mark A. Silvano, Upper Black Eddy, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days. days.

(21) Appl. No.: 15/521,762

(22) PCT Filed: Oct. 2, 2015

(86) PCT No.: PCT/US2015/053672
§ 371 (c)(1),
(2) Date: Apr. 25, 2017

(87) PCT Pub. No.: WO2016/069199
PCT Pub. Date: May 6, 2016

(65) Prior Publication Data
US 2017/0240500 A1 Aug. 24, 2017

Related U.S. Application Data

(60) Provisional application No. 62/073,285, filed on Oct. 31, 2014.

(51) Int. Cl.
| | | |
|---|---|---|
| *C07C 67/00* | (2006.01) | |
| *C07C 67/54* | (2006.01) | |
| *C07C 67/40* | (2006.01) | |
| *B01D 3/42* | (2006.01) | |
| *C02F 1/04* | (2006.01) | |
| *C02F 1/00* | (2006.01) | |
| *C02F 103/38* | (2006.01) | |

(52) U.S. Cl.
CPC .......... *C07C 67/54* (2013.01); *B01D 3/4205* (2013.01); *C02F 1/008* (2013.01); *C02F 1/04* (2013.01); *C07C 67/40* (2013.01); *C02F 2103/38* (2013.01)

(58) Field of Classification Search
CPC .......... C07C 67/39; C07C 67/54; C07C 67/40; C07C 69/54; B01D 3/4205; C02F 1/008; C02F 1/04; C02F 2103/38
See application file for complete search history.

(56) References Cited

U.S. PATENT DOCUMENTS

| | | |
|---|---|---|
| 4,249,019 A | 2/1981 | Tamura et al. |
| 4,329,513 A | 5/1982 | Aoshima et al. |
| 4,518,796 A | 5/1985 | Aoshima et al. |
| 5,883,288 A | 3/1999 | Iffland et al. |
| 5,892,102 A | 4/1999 | Mikami et al. |
| 5,969,178 A | 10/1999 | Okamoto et al. |
| 6,040,472 A | 3/2000 | Yamamatsu et al. |
| 6,107,515 A | 8/2000 | Yamaguchi |
| 7,569,721 B2 | 8/2009 | Patterson et al. |
| 2008/0160307 A1 | 7/2008 | Bauchet et al. |
| 2016/0068464 A1* | 3/2016 | Krill ............... C07C 45/75 560/208 |

OTHER PUBLICATIONS

Baohe Wang et al., Journal of Molecular Catalysis A: Chemical 379 (2013) 322-326.
Baohe Wang et al., Ing. Eng. Chem. Reg. 2012, 51, 3932-3938.

* cited by examiner

*Primary Examiner* — Yevgeny Valenrod
*Assistant Examiner* — Blaine G Doletski
(74) *Attorney, Agent, or Firm* — Husch Blackwell LLP

(57) ABSTRACT

A process for removing water from an oxidative esterification reactor includes (a) conducting an oxidative esterification reaction in a reactor; (b) removing a crude product stream from the reactor; (c) passing a first portion of the crude product stream directly to a product recovery zone; (d) introducing a second portion of the crude product stream to a distillation column to generate a column overheads stream and a column bottoms stream; (e) passing at least a portion of the columns bottoms stream to the product recovery zone; and (f) recycling a recycle stream comprising at least a portion of the overheads stream to the reactor; wherein the recycle stream contains less than 1 weight percent (wt %) water based on the total weight of the recycle stream, wherein the weight ratio of the first portion to the second portion is at least 1:10, and wherein the amount of the recycle stream recycled to the reactor is such that the reactor contains less than or equal to 2.5 wt % water, based on the weight of the reactor contents.

10 Claims, 1 Drawing Sheet

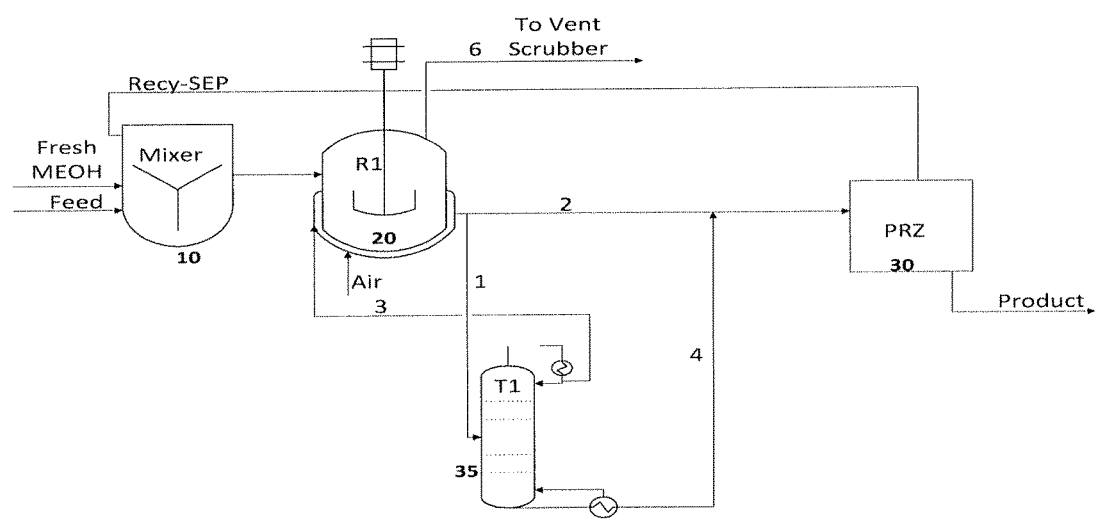

US 9,963,419 B2

PROCESS FOR IN SITU WATER REMOVAL FROM AN OXIDATIVE ESTERIFICATION REACTION USING A COUPLED REACTOR-DISTILLATION SYSTEM

BACKGROUND OF THE INVENTION

Methyl methacrylate (MMA) is an important chemical used as a starting material in the production of various products, including, among other things, acrylic plastics. One cost-efficient method for producing MMA starts with converting ethylene to propionaldehyde, followed by condensation to form methacrolein (MAL), and subsequent oxidative esterification to form MMA, with water produced as a by-product during oxidative esterification. For the oxidative esterification, the MAL is reacted with molecular oxygen in an alcohol (such as methanol) typically in the presence of a Pd-containing catalyst.

The water produced in the reactor during the oxidative esterification of methacrolein to MMA is believed to have a detrimental effect on conversion and selectivity by interacting with the Pd-containing catalyst used in the oxidative esterification reaction, as indicated in U.S. Pat. No. 6,107,515. Some of the water produced competes with the methanol to react with the MAL, thus affecting the selectivity. Also, water has a tendency to get adsorbed on the active site of the catalyst, thereby reducing the reaction rate as the concentration of water increases (reduced conversion). Recent studies on porous styrene-divinylbenzene copolymer catalyst supports (hydrophobic material with large surface area) for MAL oxidative esterification also suggests that water removal can be critical for the oxidative esterification reactor performance. (See, Wang, B., et al., *Journal of Molecular Catalysis A: Chemical*, 2013, 379(0), pp. 322-326; and Wang B. et al., *Ind. Eng. Chem. Res.*, 2012, 51(10), pp. 3932-3938.)

To remove water from the oxidative esterification reaction, published methods, such as that described in U.S. Pat. No. 6,107,515 use membranes to continuously remove water from the reaction system. However, membranes are not practical due to low separation fluxes (because of low feed concentrations and temperatures) and extremely high membrane areas that would be required. The continuous removal of water by hydrophilic membranes is thus best suited for small batch reactors and not for commercial scale.

It is desirable to develop a process for the commercial production of MMA by the oxidative esterification of MAL in which water is continuously removed from the reaction in situ.

SUMMARY OF THE INVENTION

In an embodiment, a process for removing water from an oxidative esterification reactor includes: (a) conducting an oxidative esterification reaction in a reactor; (b) removing a crude product stream from the reactor; (c) passing a first portion of the crude product stream directly to a product recovery zone; (d) introducing a second portion of the crude product stream to a distillation column to generate a column overheads stream and a column bottoms stream; (e) passing at least a portion of the columns bottoms stream to the product recovery zone; and (f) recycling a recycle stream comprising at least a portion of the overheads stream to the reactor; wherein the recycle stream contains less than 1 weight percent (wt %) water based on the total weight of the recycle stream, wherein the weight ratio of the first portion to the second portion is at least 1:10, and wherein the amount of the recycle stream recycled to the reactor is such that the reactor contains less than or equal to 2.5 wt % water, based on the weight of the reactor contents.

BRIEF DESCRIPTION OF THE DRAWINGS

FIG. 1 illustrates an exemplary reactor/distillation column configuration.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). It is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. For ranges containing explicit values (e.g., 1 or 2, or 3 to 5, or 6, or 7) any subrange between any two explicit values is included (e.g., 1 to 2; 2 to 6; 5 to 7; 3 to 7; 5 to 6; etc.).

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

Alcohol

One or more alcohols may be used in the present process. Typically the alcohol is an aliphatic alcohol, aromatic alcohol or mixture of these alcohols. In the production of a (meth)acrylic acid ester, the alcohol may be selected from the group consisting of methanol, ethanol, n-butanol, 2-ethylhexanol and combinations thereof. The corresponding esters, e.g., methyl methacrylate, methyl acrylate, ethyl acrylate, butyl acrylate, 2-ethylhexyl acrylate, respectively, are obtained.

In an embodiment, the alcohol is methanol (MeOH).

Aldehyde

The aldehyde used in the present process is selected from the group consisting of methacrolein, acrolein, and combinations thereof. In an embodiment, the aldehyde is selected from the group consisting of methacrolein and acrolein.

In an embodiment, the aldehyde is methacrolein (MAL).

Oxygen

Oxygen used in the present process can be in the form of molecular oxygen or as a mixed gas in which oxygen is diluted with a second gas which is inert to the reaction. Examples of diluent gases include nitrogen, carbonic acid gas, and air. The oxygen-containing gas may be enriched air having a higher oxygen concentration than air, or can be pure oxygen. The quantity of oxygen present in the reaction system advantageously is not less than the stoichiometric quantity required for the reaction, and preferably is not less than 1.2 times the stoichiometric quantity. In one embodiment, the amount of oxygen present is from 1.2 to 2 times the stoichiometric quantity required. Hydrogen peroxide may be introduced into the system as an oxidizer. The oxygen-containing gas can be introduced to the reaction system by any suitable means, as known by those skilled in the art. For example, the oxygen-containing gas can be introduced via a sparger or a pipe into a reactor. The simple method of blowing the oxygen-containing gas into the reaction system can be employed.

Catalyst

The catalysts used in the present process are those typically used in oxidative esterification reaction, such as palladium (Pd)-containing catalysts, including palladium-containing supported catalysts. In an embodiment, the catalyst is a supported palladium- and lead (Pb)-containing catalyst. Additional elements which may be included in a palladium-containing catalyst include, but are not limited to, Hg, Tl, Bi, Te, Ni, Cr, Co, Cd, In, Ta, Cu, Zn, Zr, Hf, W, Mn, Ag, Re, Sb, Sn, Rh, Ru, Ir, Pt, Au, Ti, Al, B, and Si.

In an embodiment, the catalyst carrier is selected from the group consisting of silica, alumina, silica-alumina, zeolite, magnesia, magnesium hydroxide, titania, calcium carbonate, and activated carbon.

Process

In an embodiment, the present process includes conducting an oxidative esterification reaction in a reactor. The oxidative esterification process is well known. See, e.g., U.S. Pat. No. 5,969,178; U.S. Pat. No. 6,107,515; U.S. Pat. No. 6,040,472; U.S. Pat. No. 5,892,102; U.S. Pat. No. 4,249,019; and U.S. Pat. No. 4,518,796.

Various reactors may be used in the present process, such as, for example, a continuous stirred tank reactor, a bubble column reactor or a fixed bed reactor. The reactor can be stirred or not stirred, and may have a mobile catalyst that generally moves with the reaction liquid, or may contain a fixed bed of catalyst through which the reaction fluid flows. Recycling of the reaction fluids through the reactor can be conducted in any of these configurations. The reaction may be conducted in a batch, semi-batch or continuous manner.

In an embodiment, the reaction is carried out in the slurry phase. The catalyst may then be separated from the product mixture, for example, by filtration or decantation. In various embodiments, the "reaction fluid," which may be a heterogeneous catalyst, e.g., slurry, or at least a portion of the reaction fluid may contact a fixed bed of catalyst during the process.

In an embodiment, the process includes producing methyl methacrylate by an esterification reaction between MAL and methanol. The process for producing MMA by an esterification reaction between MAL and methanol is not particularly limited, and may comprise any of a suitable gas phase or liquid phase or slurry phase reaction. How to carry out the reaction is also not particularly limited, and the reaction may be carried out in any of a continuous or batch manner. For example, there can be given a process comprising carrying out the reaction using a palladium based catalyst in a liquid phase in a continuous manner.

In an embodiment, the reaction may be conducted using a slurry of catalyst in the liquid phase of the reactor or reaction zone.

In an embodiment, a single reactor with a single reaction zone is used in the process. In another embodiment, multiple reactors or reaction zones are used in the process. In an embodiment, at least one reactor used in the process is a continuous stirred tank reactor (CSTR).

In an embodiment, a single reactor with a single reaction zone is used.

In an embodiment, the single reactor is a CSTR.

In an embodiment, the oxidative esterification reaction is run under oxidative reaction conditions. Oxidative reaction conditions include, for example, the oxygen partial pressure, reaction total pressure, temperature, concentration of reactants, pH and reaction time suitable to produce the desired reaction product. The specific conditions of any reactor used in this process are not particularly limiting and are selected based on the specific reactants and product created using the process.

In an embodiment, the oxygen partial pressure varies depending on the reactants, reaction conditions and type of reactor. In an embodiment, the oxygen partial pressure on the outlet side of the reactor is a positive pressure of less than or equal to 0.4 kg/cm$^2$ (5 psia). In an embodiment, the oxygen partial pressure on the outlet side of the reactor is a positive pressure of less than or equal to 2.0 kg/cm$^2$ (28 psia). When the oxygen partial pressure is too low, aldehyde conversion decreases, resulting in increased by-products.

In an embodiment, the reaction may be conducted at reduced pressure, at atmospheric pressure, or at super atmospheric pressure. The reaction total pressure for oxidative esterification reactions is typically selected within a range at which the catalyst is active for oxidative esterification reactions. Typically, however, the reaction pressure is in the range of 0.5 kg/cm$^2$ to 20 kg/cm$^2$ (7 psia to 280 psia), or preferably 1 kg/cm$^2$ to 10 kg/cm$^2$ (14 psia to 140 psia).

In an embodiment, the reaction may be conducted at a temperature of from 0° C. to 120° C., or from 40° C. to 90° C.

In an embodiment, the pH of the reaction is maintained in the range of 6 to 9. If necessary to maintain the pH, an alkali metal compound or alkaline earth metal compound may be added to the reaction. Exemplary alkaline earth metal compounds include, but are not limited to, oxides, hydroxides, carbonates, and carboxylic acid salts.

The reaction time varies depending on the reaction conditions, reactants and other factors which may influence the reaction. Typically, however, the reaction time is from 0.5 to 20 hours. For a continuous process, such as in embodiments using a CSTR, the reaction time (residence time) is governed by the kinetics of the system as determined by the pressure, temperature and catalyst used.

In an embodiment, the ratio of alcohol (e.g., methanol) fed into the reaction to aldehyde (e.g., methacrolein) fed in the reaction is not particularly limited. The reaction may be conducted over a wide range of alcohol to aldehyde molar ratios, such as 1:10 to 1,000:1, preferably from 1:2 to 50:1, more preferably from 2:1 to 15:1. In an embodiment, the alcohol is methanol, the aldehyde is methacrolein, and the molar ratio of methanol fed into the reaction to methacrolein fed into the reaction is 1:10 to 1,000:1, or 1:2 to 50:1, or 21: to 15:1.

The catalyst is employed in a catalytic amount. The amount of catalyst typically varies depending on the exact reactants, method of preparing the catalyst, composition of the catalyst, process operating conditions, reactor type, and the like, although the weight ratio of catalyst to the starting aldehyde is generally from 1:1000 to 20:1. Advantageously, the ratio of catalyst to aldehyde is from 1:100 to 4:1. However, the catalyst may be used in an amount outside these ranges.

In an embodiment, a polymerization inhibitor may be employed in the process when the product is a polymerizable compound. A wide variety of inhibitors are known and commercially available. Examples of inhibitors include hydroquinone (HQ), phenothiazine (PTZ), the methyl ester of hydroquinone (MEHQ), 4-hydroxy-2,2,6,6-tetramethylpiperidine-n-oxyl (4-hydroxy TEMPO, or 4HT), methylene blue, copper salicylate, copper dialkyldithiocarbamates, and the like.

In an embodiment, the present process includes removing a crude product stream from the reactor. The crude product typically contains target product ((meth)acrylic acid ester) along with unreacted starting material (e.g., alcohol, aldehyde) and byproducts (including water). In an embodiment, the crude product stream comprises MMA (target product) along with unreacted methanol and methacrolein, as well as an amount of water generated as a by-product. Methacrylic acid (MAA) is also generated as a by-product in the formation of MMA. MMA could also be present in the form of its salt, such as NaMAA when alkaline compounds (such as NaOH) are used to maintain the pH of the reaction. In an embodiment, additional by-products may be present in the product stream in low concentrations (minor components such as methyl formate (Me-Form)).

In an embodiment, the present process includes passing a first portion of the crude product stream directly to a product recovery zone. By passing a portion of the crude product stream to a product recovery zone, the desired product or products (e.g., MMA) are removed from the reaction zone for further purification. For example, in an embodiment, the reactants and products, as well as the desired and undesired products, are separated from the first portion of the crude product stream.

In an embodiment, the present process includes introducing a second portion of the crude product stream to a distillation column to generate a column overheads stream and a column bottoms stream.

In an embodiment, the distillation column is in fluid communication with the reactor such that it can receive, directly or indirectly, the second portion of the crude product stream. In an embodiment, the reactor is a continuous stirred tank reactor, and the distillation column is connected to the reactor such that the feed to the distillation column is a part of the reactor exit stream, and the overheads of the column is directly recycled back to the reactor (or, in an embodiment, to a previous reactor). The distillation column is thus coupled to the reactor, meaning the distillation column parameters affect the kinetics of the reaction in the reactor (or previous reactor).

The distillation column may be operated at different conditions depending on the specific oxidative esterification reaction (e.g., starting materials, reaction conditions) and should not be construed as limiting. For example, in an embodiment, the distillation column may be operated at different pressures, reflux ratios and distillate to feed ratios in order to maximize water removal from the overheads stream.

In an embodiment for the oxidative esterification of MAL to form MMA, the distillation column is operated around 1 bar to 10 bar, or 1 to 4 bar. In an embodiment, the operating reflux ratio is 0.1 to 10, or 0.5 to 3, or close to 1. In embodiments, the operating reflux ratio may be greater than 1 to achieve a better split fraction on the components; however, a higher reflux ratio requires more energy.

In an embodiment, the amount of crude product going to the product recovery zone (e.g., amount of first portion of crude product stream) and the amount of crude product going to the distillation column (e.g., amount of second portion of crude product stream) is controlled using a control valve or other available method.

In an embodiment, the weight ratio of the first portion of the crude product stream (i.e., the amount of the crude product stream going to the product recovery zone) to the second portion of the crude product stream (i.e., the amount of the crude product stream going to the distillation column) is at least 1:10. In an embodiment, the weight ratio of first portion of crude product stream to second portion of crude product stream is from 1:10 to 1:1, or from 1:8 to 1:2.

In an embodiment, the overheads stream contains primarily unreacted methanol and methacrolein with very little (less than or equal to 1 wt %) water. Some amount of MMA is also present in the overheads stream due to the formation of azeotropes, such as, for example an MeOH-MMA azeotrope (methanol-MMA azeotrope) along with an excess of methanol in the process stream.

In an embodiment, the bottoms stream contains primarily MMA. Most of the water from the crude product stream that is fed to the distillation column is split to the bottoms stream. The bottoms stream may be a single stream or a two-phase stream that can be further split to an organic stream and an aqueous stream.

In an embodiment, the present process includes passing at least a portion of the column bottoms stream to the product recovery zone and recycling at least a portion of the column overheads stream into the reaction.

In an embodiment, the present process includes passing at least a portion of the column bottoms stream to the product recovery zone and recycling at least a portion of the column overheads stream to the reactor or, in embodiments, to a previous reactor.

In an embodiment, the present process includes passing at least a portion of the column bottoms stream to the product recovery zone and recycling at least a portion of the column overheads stream to the reactor.

In an embodiment, the recycled stream (portion of the overheads stream returned to the reactor) contains less than or equal to 1 wt % water, or less than 1 wt % water based on the total weight of the portion of the overheads stream. Typically there is some amount of water remaining in the recycled stream. In an embodiment, the recycled stream contains from greater than 0 wt % to less than or equal to 1 wt % water, or from greater than 0 wt % to less than 1 wt % water, based on the total weight of the portion of the overheads stream.

By controlling (1) the amount of crude product stream introduced to the distillation column and/or (2) the amount of overheads stream recycled to the reactor, the amount of water present in the reactor is controlled to be no more than 2.5 weight percent (wt %) based on the total contents of the reactor. Without distillation, the water concentration in the reactor is typically around 3 wt % to 4 wt %. Using the present process, the water concentration in the reactor is maintained at less than or equal 2.5 wt %, or less than or equal to 2 wt %, or less than or equal to 1.5 wt %, or less than or equal to 1 wt %. In an embodiment, the water concentration in the reactor is between 1 wt % and 1.5 wt %. The decreased water content results in an increased conversion and selectivity.

In an embodiment, the process includes changing the weight ratio of first portion of crude product stream to second portion of crude product stream. When the ratio is low (e.g., about 1:10), less crude product stream is going to the product recovery zone and more crude product stream is going to the distillation column. More crude product to the distillation columns means more water is ultimately removed, resulting in a lower water content in the reactor. In contrast, if the ratio of first portion of crude product stream to second portion of crude product stream is closer to 1:1, a larger portion of the crude product is going to the product recovery zone and less crude product is going to the distillation column. As a result, less water is removed from the reaction and the water content in the reactor will be higher.

The initial distillation setup can also be tailored to optimize water removal from the crude product going to the distillation column. For example, it will be appreciated that any of the main design variables (e.g., reflux ratio, temperature, number of stages, distillate to feed fraction, bottoms to feed fraction, and/or column pressure) may be varied according to known methods to optimize split.

When using a continuous stirred tank reactor system, the water concentration throughout the reactor is the same as the water concentration at the outlet of the reactor. Water concentration can therefore be monitored using general concentration analysis methods, including, but not limited to, Karl Fischer titration or gas chromatography (GC).

Distillation is not typically used with oxidative esterification reactions to remove water due to the presence of multiple azeotropes. However, it was unexpectedly discovered that distillation of at least a portion of the crude product stream successfully removed at least some of the water from the crude product stream such that when at least a portion of the resulting overheads stream was returned (e.g., recycled) back to the reactor, the overall water concentration of the reactor is successfully decreased to less than or equal to 2.5 wt %, based on the total weight of the reactor contents. In other words, the water generated during oxidative esterification is surprisingly removed substantially contemporaneously with its generation (in situ) using distillation and charging a portion of the distilled crude product back into the system. The recycle loop between the distillation column and the reactor controls the water concentration in the single reaction zone system. Without being bound to any additional theory, the decreased water content advantageously improves the overall conversion and the selectivity of the catalyst.

FIG. 1 illustrates an exemplary reactor/distillation column configuration as used in the present process. In the embodiment shown, fresh reactants (e.g., alcohol, aldehyde and catalyst) are introduced to an optional mixer 10 before being passed to a reactor 20. Oxygen (e.g., air) is introduced to the reactor 20, and the reactor 20 may be vented through pathway 6 to a scrubber. A first portion of the crude product is transferred to the product recovery zone 30 via pathway 2. A second portion of the crude product is transferred to the distillation column 35 via pathway 1 (pumparound loop). At least a portion of the column bottoms stream is sent to the product recovery zone 30 via pathway 4 and at least a portion of the column overheads stream is recycled back to the reactor 20 via pathway 3. Unreacted starting material(s) separated from the product at the product recovery zone 30 may be recycled back to the mixer 10.

Product

The present process is used to prepare (meth)acrylic esters, such as methyl methacrylate, methyl acrylate, ethyl acrylate, butyl acrylate, 2-ethylhexyl acrylate and combinations thereof.

In an embodiment, the present process is used to prepare MMA.

Specific Embodiments of the Invention

The following examples are given to illustrate the invention and should not be construed as limiting its scope.

Azeotrope Identification

Azeotropic temperatures and compositions at atmospheric pressure are obtained using the regressed vapor liquid equilibrium (VLE) parameters for the non-random two liquid (NRTL) activity coefficient model for physical property estimation to determine the feasibility of distillation to remove water from the reaction system. Accurate representation of the phase equilibrium is developed using a non-random two liquid activity coefficient (NRTL) phase equilibrium model by regression of literature phase equilibrium data, including data sets for binary and ternary systems. For this work, reported azeotropes for the system from multiple sources (Dortmund databank datasets [4245, 6118, 19710] and Asahi patent U.S. Pat. No. 5,969,178) are used to regress VLE binary parameters using property data regression module in Aspen Plus 8.0 which is commercially available. The azeotropic data calculated using the regressed model parameters is compared to the reported azeotropic data provided in Table 1, below. The table shows good agreement between the predicted and reported azeotropic data.

TABLE 1

Azeotropic Temperatures and Compositions

| | | | Predicted Mole Fractions | | | | Reported Mole Fractions/Temperature | | | | |
|---|---|---|---|---|---|---|---|---|---|---|---|
| Temp (C.) | Type | No. Comp. | H$_2$O | MeOH | MAL | MMA | Temp (C.) | H$_2$O | MeOH | MAL | MMA |
| 59.15 | Homogeneous | 2 | | 0.50 | 0.50 | | 58.0 | | 0.46 | 0.54 | |
| 63.25 | Heterogeneous | 2 | 0.23 | | 0.77 | | 63.8 | 0.24 | | 0.76 | |
| 64.51 | Homogeneous | 2 | | 0.98 | | 0.02 | 64.3 | | 0.97 | | 0.03 |
| 81.64 | Heterogeneous | 2 | 0.50 | | | 0.50 | 81.6 | 0.5 | | | 0.5 |

To determine the efficiency of distillation, a 50 tray distillation apparatus is used with an incoming feed composition having a composition as described in Table 2, below. The reflux ratio is 0.95, with a distillate to feed ratio of 0.71. The column is run at atmospheric pressure with a temperature at the top of the column of 61° C. and a bottom temperature of 77.55° C.

TABLE 2

Feed Composition (wt %)

| | |
|---|---|
| $H_2O$ | 4.5 wt % |
| MeOH | 51.0 wt % |
| Me-Form | 1.0 wt % |
| MAL | 10.0 wt % |
| MMA | 32.5 wt % |
| NaMAA | 1.0 wt % |

The composition of the overheads stream is shown in Table 3, below. The bottoms stream is split into an organic stream and an aqueous stream, the compositions of which are described below in Tables 4 and 5.

TABLE 3

Overheads Stream Composition (wt %)

| | |
|---|---|
| $H_2O$ | 0.15 wt % |
| MeOH | 70.95 wt % |
| Me-Form | 1.0 wt % |
| MAL | 12.5 wt % |
| MMA | 15.4 wt % |
| NaMAA | 0 wt % |

TABLE 4

Organic Bottoms Stream Composition (wt %)

| | |
|---|---|
| $H_2O$ | 1.16 wt % |
| MeOH | 0.70 wt % |
| Me-Form | 0 wt % |
| MAL | 0.03 wt % |
| MMA | 97.60 wt % |
| NaMAA | 0 wt % |

TABLE 5

Aqueous Bottoms Stream Composition (wt %)

| | |
|---|---|
| $H_2O$ | 76.87 wt % |
| MeOH | 4.42 wt % |
| Me-Form | 0 wt % |
| MAL | 0 wt % |
| MMA | 1.22 wt % |
| NaMAA | 17.43 wt % |

The overheads stream contains very little water and can therefore be recycled to the reactor. The organic bottoms stream contains a majority amount (97.60 wt %) final product (MMA). The aqueous bottoms stream contains a majority amount (76.87 wt %) water. Removing the bottoms stream to a recovery zone therefore (1) recovers a portion of final product (MMA) and (2) prevents a portion of water from returning to the reactor.

ASPEN PLUS flowsheet modeling is used to guide the design of the coupled reactor-distillation water removal system and to understand the effect of process and design variables on the water concentration in the oxidative esterification reactor. A RSTOIC model or a CSTR model for a reactor and RADFRAC model for distillation is assumed in ASPEN PLUS. Within ASPEN Plus, RStoic models are used to simulate a stoichiometric reactor with specified reaction extent or conversion. RStoic is used to model a reactor when reaction kinetics are unknown or unimportant and stoichiometry and the molar extent or conversion is known for each reaction. RStoic can model reactions occurring simultaneously or sequentially. In addition, RStoic can perform product selectivity and heat of reaction calculations. RADFRAC module for distillation has the ability to simulate phase equilibria simultaneously with chemical equilibria or with incorporation of reaction kinetic data. The details of the RADFRAC algorithm used for simulation of reactive distillation systems are described in detail by Venkataraman et al., Reactive Distillation using ASPEN Plus., Chem. Eng. Prog., (1990), 69, 45-54. ASPEN Plus is further supported by a strong physical and chemical properties database, including hydrodynamics of column packings and the ability to predict properties of components not present in the database. Specifying either the kinetics or the conversion/residence time for the reactor and specifying the appropriate design variables for the distillation column (reflux ratios, stages and column pressures), the process for water removal using a coupled reactor-distillation system can be simulated. Regressed property parameters described above are used for each of the reactor and distillation models.

The weight ratio of first portion of crude product stream to second portion of crude product stream is a key design variable that is varied. When the ratio is low (e.g., about 1:10), less crude product stream is going to the product recovery zone and more crude product stream is going to the distillation column. More crude product to the distillation columns means more water is ultimately removed from the reaction zone through the distillation column bottom stream, resulting in a lower water content in the recycle stream returning to the reactor, and hence, a lower water content in the reactor. In contrast, if the ratio of first portion of crude product stream to second portion of crude product stream is closer to 1:1, a large portion of the crude product is going to the product recovery zone and less crude product is going to the distillation column. As a result, less water is removed from the reaction zone and the water content in the reactor will be higher. This indicates that a lower ratio of the first portion to the second portion is desired to maintain lower water concentration in the reactor; however, in this scenario, since a large fraction of the stream is entering the distillation column, the size and energy requirement of the distillation column would be very high. With increase in the above described ratio, the size and energy requirement of the distillation column reduces. Hence, the water content in the reactor has an inverse relationship with the size and energy requirement of the distillation column.

The invention claimed is:

1. A process for removing water from an oxidative esterification reactor, the process comprising: (a) conducting an oxidative esterification reaction in a reactor; (b) removing a crude product stream from the reactor; (c) passing a first portion of the crude product stream directly to a product recovery zone; (d) introducing a second portion of the crude product stream to a distillation column to generate a column overheads stream and a column bottoms stream; (e) passing at least a portion of the columns bottoms stream to the product recovery zone; and (f) recycling a recycle stream comprising at least a portion of the overheads stream to the reactor; wherein the recycle stream contains less than 1 weight percent (wt %) water based on the total weight of the recycle stream, wherein the weight ratio of the first portion to the second portion is at least 1:10, and wherein the amount of the recycle stream recycled to the reactor is such that the reactor contains less than or equal to 2.5 wt % water, based on the weight of the reactor contents.

2. The process of claim 1 wherein the conducting an oxidative esterification reaction in a reactor comprises contacting, under oxidative esterification conditions, an alcohol, an aldehyde and oxygen.

3. The process of claim 1 wherein the weight ratio of the first portion to the second portion is from 1:10 to 1:1.

4. The process of claim 1 wherein the weight ratio of the first portion to the second portion is controlled such that the reactor contains between 1 wt % and 1.5 wt % water based on the weight of the reactor contents.

5. A process for removing water from an oxidative esterification reactor, the process comprising: (a) conducting an oxidative esterification reaction in a reactor; (b) removing a crude product stream from the reactor; (c) passing a first portion of the crude product stream directly to a product recovery zone; (d) introducing a second portion of the crude product stream to a distillation column to generate a column overheads stream and a column bottoms stream; (e) passing at least a portion of the columns bottoms stream to the product recovery zone; (f) recycling a recycle stream comprising at least a portion of the overheads stream to the reactor; and (g) controlling the amount of water in the reactor such that the reactor contains less than or equal to 2.5 wt % water based on the weight of the reactor contents; wherein the recycle stream contains less than 1 weight percent (wt %) water based on the total weight of the recycle stream, and wherein the weight ratio of the first portion to the second portion is 1:10 to 1:1.

6. The process of claim 5 wherein the step of controlling the amount of water in the reactor comprises changing the weight ratio of the first portion to the second portion.

7. The process of claim 6 wherein the changing the weight ratio of the first portion to the second portion comprises decreasing the weight ratio to increase the amount of crude product stream passed to the distillation column.

8. The process of claim 6 wherein the changing the weight ratio of the first portion to the second portion comprises increasing the weight ratio to decrease the amount of crude product stream passed to the distillation column.

9. The process of claim 5 wherein the step of controlling the amount of water in the reactor comprises controlling the amount of the overheads stream recycled to the reactor.

10. The process of claim 5 wherein the step of controlling the amount of water in the reactor comprises adjusting operating details of the distillation column selected from the group consisting of reflux ratio, temperature, number of stages, distillate to feed fraction, bottoms to feed fraction, column pressure and combinations thereof.

* * * * *